United States Patent
Weisgraber et al.

(10) Patent No.: US 7,432,355 B2
(45) Date of Patent: Oct. 7, 2008

(54) APOLIPOPROTEIN E STABLE FOLDING INTERMEDIATE AND METHODS OF USE THEREOF

(75) Inventors: Karl H. Weisgraber, Walnut Creek, CA (US); Julie A. Morrow, Oakland, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 716 days.

(21) Appl. No.: 10/626,415

(22) Filed: Jul. 23, 2003

(65) Prior Publication Data

US 2004/0228851 A1 Nov. 18, 2004

Related U.S. Application Data

(60) Provisional application No. 60/402,470, filed on Aug. 9, 2002.

(51) Int. Cl.
*C07K 14/00* (2006.01)
*A61K 38/48* (2006.01)

(52) U.S. Cl. ............ 530/359; 530/361; 424/94.63

(58) Field of Classification Search ............ 435/4; 424/9.1, 283.1, 569, 570, 94.63; 530/359, 530/361
See application file for complete search history.

(56) References Cited

U.S. PATENT DOCUMENTS

| | | | | |
|---|---|---|---|---|
| 6,022,683 | A | * 2/2000 | Poirier | 435/4 |
| 6,027,896 | A | * 2/2000 | Roses et al. | 435/6 |
| 6,322,802 | B1 | 11/2001 | Prusiner et al. | |
| 6,331,296 | B1 | 12/2001 | Prusiner et al. | |

2002/0009439 A1 1/2002 Mahley et al.

OTHER PUBLICATIONS

Morrow et al, Biochemistry vol. 39(38), pp. 11657-11666, (Sep. 2000)(Abstract Only).*
Barrick et al., "Three-State Analysis of Sperm Whale Apomyoglobin Folding" (1993) Biochemistry, 32(14), 3790-3796.*
Huang et al. (2001) *Proc. Natl. Acad. Sci. USA* 98:8838-8843.
Ji et al. (2002) J. Bio. Chem. 277:21821-21828.
*Proc. Natl. Acad. Sci. USA* 93:15051-15056.
Morrow, et al., Differences In Stability Among the Human Apollpoportein E Isoforms Determined by the Amino-Terminal Domain. Biochemistry, Sep. 26, 2000, vol. 39, No. 38, pp. 11657-11666.
Acharya et al., (2001) Thermal Denaturation Studies of the Isoforms of Human Apolipopotein E, Biophys. J., vol. 80, p. 147a.
Morrow et al., (2002) Apolipoprotein E4 Forms a Molten Globule, J. Biol. Chem., vol. 277, p. 50380-50385.
Pillot et al., (1997) Specific modulation of the fusogenic properties of the Alzheimer β-amyloid peptide by apolipoprotein E isoforms, Eur. J. Biochem., vol. 243, pp. 650-659.
Fink, A. Methods in Molecular Biology, vol. 40: Protein Stability and Folding: Theory and Practice, Edited by B. A. Shirley. 1995, Chapter 15: Molten Globules, pp. 343-360. Humana Press Inc., Totowa NJ.

* cited by examiner

*Primary Examiner*—Jon P Weber
*Assistant Examiner*—Kailash C Srivastava
(74) *Attorney, Agent, or Firm*—Paula A. Borden; Bozicevic, Field & Francis LLP

(57) ABSTRACT

The present invention provides isolated apolipoprotein E (apoE) stable folding intermediates. The invention further provides methods for identifying compounds that alter the structure or level or activity of an apoE stable folding intermediate, as well as methods of inhibiting the formation or activity of stable folding intermediates of apoE. The invention further provides methods for reducing the level and/or activity of an apoE stable folding intermediate, and methods for treating disorders relating to apoE4 in a subject.

10 Claims, 4 Drawing Sheets

Four-helix Bundle

APOLIPOPROTEIN E STABLE FOLDING INTERMEDIATE AND METHODS OF USE THEREOF

CROSS-REFERENCE

This application claims the benefit of U.S. Provisional Patent Application No. 60/402,470 filed Aug. 9, 2002, which application is incorporated herein by reference in its entirety.

STATEMENT REGARDING FEDERALLY SPONSORED RESEARCH

This invention was made with government support under grant number RO1NS35939 awarded by the National Institute of Health. The government may have certain rights in this invention.

FIELD OF THE INVENTION

This invention relates to molten globule formation of apolipoproteins. In particular this invention relates to inhibiting molten globule formation of apolipoprotein E4.

BACKGROUND OF THE INVENTION

ApoE, a 34-kDa protein, is the product of a single gene on chromosome 19 and exists in three major isoforms designated apoE2, apoE3 and apoE4. ApoE contains two structural domains: an amino-terminal and a carboxy-terminal domain. Each domain is associated with a specific function. The amino terminal domain contains the lipoprotein receptor binding region and the carboxy-terminal domain contains the major lipid-binding elements. The two domains appear to interact with each other in an isoform-specific manner such that amino acid substitutions in one domain influence the function of the other domain, a phenomenon referred to as domain interaction. Domain interaction is responsible for the preference of apoE4 for very low density lipoproteins (VLDL) contrasted with the preference of apoE3 for high density lipoproteins (HDL).

By redistributing lipids among the cells of different organs, apoE plays a critical role in lipid metabolism. While apoE exerts this global transport mechanism in chylomicron and VLDL metabolism, it also functions in the local transport of lipids among cells within a tissue. Cells with excess cholesterol and other lipids may release these substances to apoE-lipid complexes or to HDL containing apoE, which can transport the lipids to cells requiring them for proliferation or repair. The apoE on these lipoprotein particles mediates their interaction and uptake via the LDL receptor or the LRP.

ApoE also plays a neurobiological role. ApoE mRNA is abundant in the brain, where it is synthesized and secreted primarily by astrocytes. ApoE-containing lipoproteins are found in the cerebrospinal fluid and appear to play a major role in lipid transport in the central nervous system (CNS). ApoE plus a source of lipid promotes marked neurite extension in dorsal root ganglion cells in culture and ApoE levels dramatically increase (about 250-fold) after peripheral nerve injury. ApoE appears to participate both in the scavenging of lipids generated after axon degeneration and in the redistribution of these lipids to sprouting neurites for axon regeneration and later to Schwann cells for remyelination of the new axons. ApoE has been implicated in Alzheimer's disease and cognitive performance. ApoE4 is associated with the two characteristic neuropathologic lesions of Alzheimer's disease; extracellular neuritic plaques representing deposits of amyloid beta (Aβ) peptide and intracellular neurofibrillary tangles representing filaments of hyperphosphorylated tau, a microtubule-associated protein. ApoE4 has been associated with decreased learning ability and impaired memory. ApoE4 has been found to be a risk factor of the outcome of patients designated as having memory impairment.

Alzheimer's disease is generally divided into-three categories: early-onset familial disease (occurring before 60 years of age and linked to genes on chromosomes 21 and 14); late-onset familial disease; and sporadic late-onset disease. Both types of late-onset disease have recently been linked to chromosome 19 at the apoE locus. Other results suggest that apoE4 is directly linked to the severity of the disease in late-onset families. Recently, cholesterol lowering drugs, the statins, have been suggested for use in treating Alzheimer's disease by lowering apoE4 levels.

In the case of Alzheimer's disease alone, approximately 4 million individuals are affected in the United States. With the aging of the population, this number is projected to triple in the next twenty years. There are currently no effective therapies for arresting (and, more importantly, reversing) the impairment of central and peripheral nervous system function once an irreversible degenerative cascade begins. Likewise, there is no current therapy for restoration of normal, central and peripheral nervous system function when the induced stress has a less catastrophic or partially reversible effect compared to the dementias.

There is a need in the art for compositions and methods for treating apoE4-related disorders, such as AD and disorders related to serum lipids. The instant invention addresses this need.

Literature

Huang et al. (2001) Proc. Natl. Acad. Sci. USA 98:8838-8843; Ji et al. (2002) J. Bio. Chem. 277:21821-21828; Proc. Natl. Acad. Sci. USA 93:15051-15056; U.S. Pat. Nos. 6,046,381; 6,331,296; and 6,322,802.

SUMMARY OF THE INVENTION

The present invention provides isolated apolipoprotein E (apoE) stable folding intermediates. The invention further provides methods for identifying compounds that alter the structure, level, or activity of an apoE stable folding intermediate, as well as methods of inhibiting the formation or activity of apoE stable folding intermediates. The invention further provides methods for reducing the level and/or activity of an apoE stable folding intermediate, and methods for treating disorders relating to apoE4 in a subject.

Features of the Invention

The present invention features a composition that includes an isolated apoE stable folding intermediate. The stable folding intermediate can be of any apoE isotype, e.g., apoE2, apoE3, or apoE4. In some embodiments, the stable folding intermediate is an apoE4 stable folding intermediate. In some embodiments, the apoE stable folding intermediate comprises an N-terminal fragment of apoE4. In some of these embodiments, the N-terminal fragment of apoE4 is about 22 kDa in size.

The invention further features a method of identifying an agent that reduces the lipid binding activity of an apoE stable folding intermediate. The method generally involves contacting an apoE stable folding intermediate in a solution with a test agent; and (b) determining the effect, if any, of the test agent on the lipid binding activity of the apoE stable folding intermediate. In some embodiments, the solution has a pH in the range of from about 2 to about 6, e.g., a pH of about 4.0 In some embodiments, the solution comprises a denaturant. In some embodiments, the denaturant is urea in a concentration of from about 3 M to about 6 M. In some embodiments, determination of the effect of the test agent is carried out by turbidimetric analysis of clearing of a lipid-containing vesicle. The method can be carried out using a stable folding intermediate of any apoE isotype, e.g., apoE2, apoE3, or apoE4. In some embodiments, the stable folding intermediate is an apoE4 stable folding intermediate.

The invention further features a method of identifying an agent that reduces the level of an apoE stable folding intermediate. The method generally involves contacting an apoE stable folding intermediate in a solution with a test agent; and determining the effect, if any, of the test agent on the level of the apoE stable folding intermediate. In some embodiments, the determining is by far-UV circular dichroism. In other embodiments, the determining is by Fourier transform infrared spectroscopy. In other embodiments, the determining is by dynamic light scattering.

The invention further features a method of treating apoE4-related disorder. The method generally involves administering an effective amount of an agent that reduces the level and/or activity of an apoE stable folding intermediate. Examples of apoE-related disorders that can be treated include neurological diseases, such as Alzheimer's disease; and cardiovascular diseases. In some embodiments, formation of neurofibrillary tangles is inhibited.

The invention further features a variant apoE polypeptide ("stable variant apoE") that has a reduced tendency to form a stable folding intermediate, compared to a native apoE polypeptide of the same isotype. The invention further features a polynucleotide comprising a nucleotide sequence encoding a subject stable variant apoE, vectors comprising the polynucleotides, and host cells comprising the polynucleotides.

DEFINITIONS

Figure 1A:
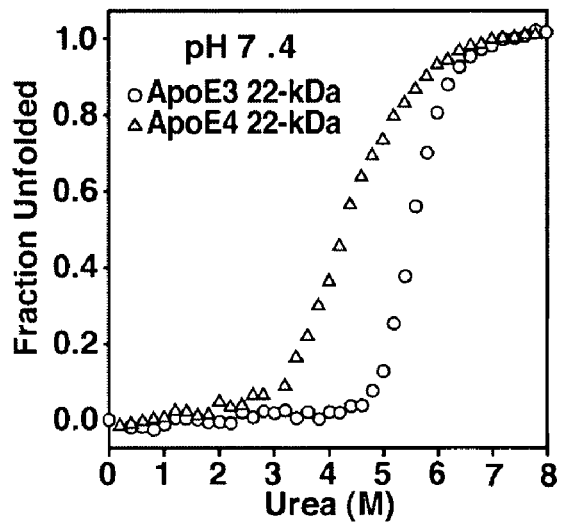
FIGS. 1A-1C depict urea denaturation of apoE3 and apoE4 22-kDa fragments.

As used herein, an "apoE4-associated disorder" is any disorder that is caused by the presence of apoE4 in a cell, in the serum, in the interstitial fluid, in the cerebrospinal fluid, or in any other bodily fluid of an individual; any physiological process or metabolic event that is influenced by apoE4 domain interaction; any disorder that is characterized by the presence of apoE4; a symptom of a disorder that is caused by the presence of apoE4 in a cell or in a bodily fluid; a phenomenon associated with a disorder caused by the presence in a cell or in a bodily fluid of apoE4; and the sequelae of any disorder that is caused by the presence of apoE4. ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

The term "Alzheimer's disease" (abbreviated herein as "AD") as used herein refers to a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

The terms "treatment" "treating" and the like are used herein to refer to any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an apoE molten globule" includes a plurality of such molten globules and reference to "the assay" includes reference to one or more assays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides isolated apolipoprotein E (apoE) stable folding intermediates. The invention further provides methods for identifying compounds that alter the structure of an apoE stable folding intermediate, as well as methods of inhibiting the formation or activity of molten globules of apoE. The invention further provides methods for treating disorders relating to apolipoprotein E, such as neurological or cardiovascular disease in a subject.

Stable Folding Intermediates of ApoE

The present invention provides isolated stable folding intermediates of apoE. Isolated stable folding intermediates of apoE are molten globules. ApoE stable folding intermediates are useful for identifying compounds that alter the structure and/or activity of such stable folding intermediates. Compounds so identified are useful for treating apoE4-related disorders.

ApoE stable folding intermediates of the invention include stable folding intermediates of apoE2, apoE3, and apoE4. Of particular interest in some embodiments is a stable folding intermediate of apoE4.

Isolated apoE stable folding intermediates of the invention have one or more of the following characteristics: (1) a molten globule structure; (2) near native-like structural features; (3) a significant amount of the native state secondary structure, structural compactness, and internal mobility with exposure of its hydrophobic core; (4) enhanced ability to bind lipid.

ApoE stable folding intermediates are formed in vitro under conditions of low pH and denaturation. Suitable denaturants include, but are not limited to, a chaotropic agent such as guanidinium isothiocyanate, guanidinium hydrochloride, urea, and the like; heat; sodium dodecyl sulfate; and the like. Concentrations of these denaturants are adjusted accordingly. The concentration of denaturant is determined by monitoring formation of the stable folding intermediate, using any known method, including those described below.

ApoE stable folding intermediates are formed at low pH, e.g., a pH of from about 1.0 to about 5.0, e.g., from about 1.0 to about 2.0, from about 2.0 to about 4.0, or from about 4.0 to about 5.0.

The source of apoE may be any source of apoE, such as recombinant apoE, synthetic apoE, purified apoE, modified apoE or fragments of apoE. Any apoE isoform can be used as the source of the stable intermediate, including apoE2, apoE3, and apoE4. In particular embodiments of interest, an apoE stable folding intermediate is an apoE4 stable folding intermediate. The amino acid sequences of apoE polypeptides are known in the art. See, e.g., GenBank Accession Nos. K00396; NM_000041; AF261279; and AAB59518.

ApoE is synthesized as a pre-polypeptide that is processed into a mature apoE polypeptide that is approximately 34 kDa protein of about 299 amino acids in length. "Full-length" apoE, as used herein, refers to a mature, 34 kDa protein of about 299 amino acids. The amino acid sequences of ApoE pre-polypeptide and mature polypeptides are provided in GenBank accession number AAB59518.

Full-length apoE is suitable for use in generating stable folding intermediates. Also suitable for use in generating apoE stable folding intermediates are fragments of apoE. ApoE having N-terminal truncations (compared to full-length apoE) of from 1 to about 40 amino acids and/or having C-terminal truncations (compared to full-length apoE) of from about 1 to about 140 amino acids are suitable for use, e.g., N-terminal truncations of from 1 amino acid to about 5 amino acids, from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, or from about 35 amino acids to about 40 amino acids; and/or C-terminal truncations of from about 5 amino acids, from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, from about 50 amino acids to about 75 amino acids, from about 75 amino acids to about 100 amino acids, from about 100 amino acids to about 125 amino acids, or from about 125 amino acids to about 140 amino acids.

Suitable fragments of apoE include, but are not limited to, fragments having molecular weights in the range of from about 14 kDa to about 22 kDa. In some embodiments of interest, an apoE stable folding intermediate is generated from a 22 kDa N-terminal fragment of apoE (Morrow et al. (2000) *Biochemistry* 39:11657-11666).

ApoE stable folding intermediates of the invention are isolated, e.g., less than about 40%, less than about 30%, less than about 20%, less than about 15%, less than about 10%, less than about 5%, or less than about 1% of the protein in a sample is a protein other than an apoE stable folding intermediate. For example, less than about 40%, less than about 30%, less than-about 20%, less than about 15%, less than about 10%, less than about 5%, or less than about 1% of the protein in a sample is a native apoE protein or other protein. In some embodiments, apoE stable folding intermediates are purified, e.g., are at least about 60%, at least about 70%, at least about 80%, at least about 85%, at least about 90%, at least about 95%, at least about 98%, or at least about 99% pure.

Whether a given condition or set of conditions gives rise to an apoE stable folding intermediate can be determined using any of a variety of well-known methods, including, but not limited to, far-ultraviolet circular dichroism; Fourier transform infrared spectroscopy; dynamic light scattering; and pepsin proteolysis. The purity of a sample can be determined using any of the foregoing methods.

For example, an apoE stable folding intermediate is produced in significant amounts in conditions of about 2 M to about 7M urea. As detected by far-ultraviolet (uv) circular dichroism (CD) an apoE4 stable folding intermediate is maximally abundant (i.e. approximately 90% of total apoE) in a solution of apoE at pH 4.0 in about 3.5 M to about 4.5 M urea. An apoE4 stable folding intermediate is approximately 50% abundant in about 3.0 M urea to about 6.0 M urea. Virtually no apoE4 can be detected below 2.0 M urea, at least by far-uv CD. As detected by far-uv CD, an apoE3 stable folding intermediate is maximally abundant (i.e. approximately 80% of total apoE) in a solution of apoB at pH 4.0 in about 4.5 M to about 5 M urea. An apoE3 stable folding intermediate is approximately 50% abundant in about 3.8 M urea to about 6.0 M urea. Virtually no apoE3 molten globule can be detected below 2.5 M urea, at least by far-uv CD.

In some embodiments, as measured by solution attenuated total reflectance Fourier transform infrared spectroscopy (FTIR), an apoE4 stable folding intermediate in 3.75 M urea at pH 4.0 contains approximately 61% of the native helical content, where the native helical content is 75% α-helix and 3% β-sheet and the molten globule helical content is 46% α-helix and 17% β-sheet.

In some embodiments, as measured by dynamic light scattering, an apoE stable folding intermediate in 3.75 M urea at pH 4.0 has a hydrodynamic radius of about 3.93+/−0.4 nm and a polydispersity of about 12.5%.

Stable ApoE Polypeptides

The invention provides stable apoE variants that have a reduced tendency to form stable folding intermediates compared to native apoE. A variant stable apoE has one or more amino acid changes compared to a native apoE. Stable apoE variants are useful for research purposes, e.g., to test the ability of such stable apoE variants in reducing, in an experimental animal model for apoE-associated disorders, disorders and symptoms associated with apoE. In particular, stable apoE variants are useful for testing in animal models of apoE4-related disorders. Such animal models are known in the art. See, e.g., U.S. Pat. Nos. 6,046,381; 5,767,337; and 6,1754,057. Stable variant apoE polypeptides are also useful for treating-disorders related to apoE4 in humans. A polynucleotide encoding a stable apoE variant is introduced into a human suffering from an apoE4-related disorder, and the encoded stable apoE variant is produced. Production of the stable apoE variant in the individual treats the disorder.

Stable apoE variants have a reduced tendency to adopt one or more of the following characteristics associated with apoE stable folding intermediates: (1) a molten globule structure; (2) near native-like structural features; (3) a significant amount of the native state secondary structure, structural compactness, and internal mobility with exposure of its hydrophobic core; (4) enhanced ability to bind lipid.

Whether a given variant apoE has reduced stable folding intermediate characteristics can be determined as described above, e.g., by placing the variant in conditions under which native apoE forms a stable folding intermediate; and determining the level of and/or activity associated with an apoE stable folding intermediate.

Polynucleotides

The invention further provides nucleic acids that include a nucleotide sequence that encodes a stable apoE variant polypeptide, as well as host cells that contain the nucleic acid. In some embodiments, the host cells are isolated. In other embodiments, the host cells are part of a transgenic, non-human animal that includes, as a transgene, a nucleic acid of the invention. Nucleic acids encoding stable apoE variant polypeptides are useful for producing stable apoE variant polypeptides, e.g., for in vitro testing; for testing the efficacy of such polypeptides in vivo in non-human animal models; and for gene therapy, e.g., for introduction of the stable apoE variant into an individual to treat an apoE4-related disorder.

Nucleic Acids

The subject nucleic acid molecules may be part of a vector ("construct") for use in generating a transgenic, non-human animal of the invention, as described below, or for use in generating a recombinant host cell that produces a stable variant apoE polypeptide. In addition, a nucleic acid molecule of the invention may encode all or part of a stable variant apoE polypeptide of the invention, and as such is useful, as part of an expression vector, in producing stable variant apoE polypeptide.

The sequence of the mouse apoE gene is found under Genbank accession number D00466. Various human and non-human primate apoE gene sequences are found under GenBank accession numbers AF200508, AF200507, AF200506, and AH009953 (*Hylobates lar*, or gibbon); AH009952, AF200503, AF200504, and AF200505 (*Pongo pygmaeus*, or orangutan); AH009951, AF200500, AG200501, and AF200502 (*Gorilla gorilla*); AH009950, AF200497, AF200498, AF200499 (*Pan troglodytes*, or chimpanzee); K00396, NM_000041; and AF261279 (*H. sapiens*). Any apoE-encoding sequence can be modified to form a stable apoE variant-encoding sequence.

In some embodiments, nucleic acids of the invention include the open reading frame encoding a variant stable apoE polypeptide, one or more introns, may further include adjacent 5' and 3' non-coding nucleotide sequences involved in the regulation of expression, and are generally up to about 10 kb in total length, but possibly longer. The DNA sequences encoding all or part of the recombinant apoE are genomic DNA or a fragment thereof. The apoE gene encoding a variant stable apoE may be introduced into an appropriate vector for extrachromosomal maintenance or for integration into the host.

A genomic sequence of interest comprises the nucleic acid present between the initiation codon and the stop codon, except for those nucleotides encoding carboxyl-terminal amino acids, as discussed above, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where apoE is expressed. Transcription or translational control regions are generally operably linked to stable variant apoE polypeptide-encoding apoE gene in order to promote expression of stable variant apoE or other proteins of interest in cultured cells, or in embryonic, fetal or adult tissues, and for gene therapy.

In some embodiments, regulatory elements include regulatory elements that result in neuronal cell-specific expression of the operably linked variant stable apoE-encoding nucleic acid. Neuronal cell-specific regulatory elements (including promoters, enhancers, and the like) are known to those skilled in the art. Examples of neuronal cell-specific regulatory elements include those from a neuron-specific enolase (NSE) gene (Hannas-Djebarra et al. (1997) *Brain Res. Mol. Brain Res.* 46:91-99); a PDGF gene; a Th1 gene (e.g., mouse Thy1.2 (Caroni et al. (1997) *J. Neurosci. Methods* 71:3-9); a neurofilament gene (e.g., NF-L, NF-M, and NF-L); a glial filament acidic protein gene; a myelin basic protein gene; a microtubule associated protein genes; a synaptophysin gene; a tyrosine hydroxylase gene; and the like.

In other embodiments, a nucleic acid molecule of the invention comprises a cDNA comprising sequences that encode a stable variant apoE protein of the invention. The nucleic acid compositions used in the subject invention may encode all or a part of the stable variant apoE polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nucleotides (nt), usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

In some embodiments, a nucleic acid molecule of the invention comprises nucleotide sequences of a genomic apoE gene, modified as described above such that the encoded apoE protein is a stable variant apoE polypeptide. In other embodiments, a nucleic acid molecule of the invention comprises the coding regions of a apoE gene, modified as described above such that the encoded apoE protein is a stable variant apoE polypeptide (e.g., a cDNA molecule encoding a stable variant apoE).

Subject nucleic acid molecules may comprise other, non-apoE nucleic acid molecules ("heterologous nucleic acid molecules") of any length. For example, the subject nucleic acid molecules may be flanked on the 5' and/or 3' ends by heterologous nucleic acid molecules of from about 1 nt to about 10 nt, from about 10 nt to about 20 nt, from about 20 nt to about 50 nt, from about 50 nt to about 100 nt, from about 100 nt to about 250 nt, from about 250 nt to about 500 nt, or from about 500 nt to about 1000 nt, or more in length. For example, when used as a probe to detect nucleic acid molecules capable of hybridizing with the subject nucleic acids, the subject nucleic acid molecules may be flanked by heterologous sequences of any length. Heterologous sequence include, but are not limited to, sequences encoding a reporter protein, and the like.

The subject nucleic acid molecules may also be provided as part of a vector, a wide variety of which are known in the art and need not be elaborated upon herein. Vectors include, but are not limited to, plasmids; cosmids; viral vectors; artificial chromosomes (YAC's, HAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject nucleic acid molecules are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant", i.e. flanked by one or more nucleotides with which it is not normally associated on a naturally occurring chromosome.

The subject nucleic acid compositions find use in the preparation of all or a portion of the stable variant apoE polypeptides of the invention, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject polypeptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme or other protein marker, e.g. β-galactosidase, a fluorescent protein, luciferase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, or any of the above-described fragment, and up to the complete open reading frame of the gene. After introduction of the DNA, the cells containing the construct may be selected by means of a selectable marker, the cells expanded and then used for expression.

Proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, Neuro-2A cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. A wide variety of such systems are known to those skilled in the art.

Expression constructs generally include a transcriptional control element, typically a promoter, operably linked to the coding region of interest to facilitate expression of the polynucleotide of interest. A variety of promoters are known in the art, including strong promoters active in eukaryotic cells, including a promoter from cytomegalovirus (CMV), mouse mammary tumor virus (MMTV), Rous sarcoma virus (RSV), or adenovirus. Exemplary promoters include the promoter from the immediate early gene of human CMV (Boshart et al., Cell 41:521-530, 1985); the promoter from the long terminal repeat (LTR) of RSV (Gorman et al. (1982 Proc. Natl. Acad. Sci. USA 79:6777-6781); SV40 early promoter; and the adenovirus major late promoter. Alternatively, the promoter used may be a tissue-specific promoter, a variety of which are known in the art.

Other control sequences operably linked to the polynucleotide of interest can be included. Nucleic acid "control sequences" or "regulatory elements" refer collectively to promoter sequences, ribosome binding sites, polyadenylation signals, transcription termination sequences, upstream regulatory domains, enhancers, and the like, which collectively provide for the transcription and translation of a coding sequence in a eukaryotic cell.

Other components may be included in the vector such as a marker (e.g., an antibiotic resistance gene, such as an ampicillin resistance gene, a gene encoding a green fluorescent protein or a β-galactosidase-encoding gene) to aid in selection and/or visualization of cells containing and/or expressing the construct, an origin of replication for stable replication of the construct in a bacterial cell (preferably, a high copy number origin of replication), a nuclear localization signal, or other elements which facilitate production of the expression construct, the protein encoded thereby, or both. In some embodiments, the polynucleotide will express one or more foreign proteins in the host, which foreign proteins will stimulate an immune response.

A subject polynucleotide can be delivered as a naked polynucleotide, or associated with ("complexed with") a delivery vehicle. "Associated with", or "complexed with", encompasses both covalent and non-covalent interaction of a polynucleotide with a given delivery vehicle.

Viral Delivery Vehicles

A subject polynucleotide can be associated with viral delivery vehicles. As used herein, a "viral delivery vehicle" intends that the polynucleotide to be delivered is encapsidated in a viral particle.

Numerous viral genomes useful in in vivo transformation and gene therapy are known in the art, or can be readily constructed given the skill and knowledge in the art. Included are replication competent, replication deficient, and replication conditional viruses. Viral vectors include adenovirus, mumps virus, a retrovirus, adeno-associated virus, herpes simplex virus (HSV), cytomegalovirus (CMV), vaccinia virus, and poliovirus, and non-replicative mutants/variants of the foregoing. In some embodiments, a replication-deficient virus is capable of infecting slowly replicating and/or terminally differentiated cells, since the respiratory tract is primarily composed of these cell types. For example, adenovirus efficiently infects slowly replicating and/or terminally differentiated cells. In some embodiments, the viral genome itself, or a protein on the viral surface, is specific or substantially specific for cells of the targeted cell. A viral genome can be designed to be target cell-specific by inclusion of cell type-specific promoters and/or enhancers operably linked to a gene(s) essential for viral replication.

Where a replication-deficient virus is used as the viral genome, the production of virus particles containing either DNA or RNA corresponding to the polynucleotide of interest can be produced by introducing the viral construct into a recombinant cell line which provides the missing components essential for viral replication and/or production. Preferably, transformation of the recombinant cell line with the recombinant viral genome will not result in production of replication-competent viruses, e.g., by homologous recombination of the viral sequences of the recombinant cell line into the introduced viral genome. Methods for production of replication-deficient viral particles containing a nucleic acid of interest are well known in the art and are described in, for example, Rosenfeld et al., Science 252:431-434, 1991 and Rosenfeld et al., Cell 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., J. Virol. 67:2928-2931, 1993; Takeuchi et al., Archiv. Virol., 128:177-183, 1993; Tanabayashi et al., Virol. 187:801-804, 1992; Kawano et al., Virol., 179:857-861, 1990; Elango et al., J. Gen. Virol. 69:2893-28900, 1988.

Non-Viral Delivery Vehicles

A subject polynucleotide can be administered using a non-viral delivery vehicles. "Non-viral delivery vehicle" (also referred to herein as "non-viral vector") as used herein is meant to include chemical formulations containing naked or condensed polynucleotides (e.g, a formulation of polynucleotides and cationic compounds (e.g., dextran sulfate)), and naked or condensed polynucleotides mixed with an adjuvant such as a viral particle (i.e., the polynucleotide of interest is not contained within the viral particle, but the transforming formulation is composed of both naked polynucleotides and viral particles (e.g., adenovirus particles) (see, e.g., Curiel et al. 1992 Am. J. Respir. Cell Mol. Biol. 6:247-52)). Thus "non-viral delivery vehicle" can include vectors composed of polynucleotides plus viral particles where the viral particles do not contain the polynucleotide of interest. "Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed by Felgner et al (U.S. Pat. Nos. 5,264,618 and 5,459,127; *PNAS* 84:7413-7417, 1987; *Annals N.Y. Acad. Sci.* 772:126-139, 1995); they may also consist of neutral or negatively charged phospholipids or mixtures thereof including artificial viral envelopes as disclosed by Schreier et al. (U.S. Pat. Nos. 5,252,348 and 5,766,625).

Non-viral delivery vehicles include polymer-based carriers. Polymer-based carriers may include natural and synthetic polymers and co-polymers. Preferably, the polymers are biodegradable, or can be readily eliminated from the subject. Naturally occurring polymers include polypeptides and polysaccharides. Synthetic polymers include, but are not limited to, polylysines, and polyethyleneimines (PEI; Boussif et al., *PNAS* 92:7297-7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

"Non-viral delivery vehicles" further include bacteria. The use of various bacteria as delivery vehicles for polynucleotides has been described. Any known bacterium can be used as a delivery vehicle, including, but not limited to non-pathogenic strains of *Staphylococcus, Salmonella*, and the like.

The polynucleotide to be delivered can be formulated as a DNA- or RNA-liposome complex formulation. Such complexes comprise a mixture of lipids which bind to genetic material (DNA or RNA) by means of cationic charge (electrostatic interaction). Cationic liposomes which may be used in the present invention include 3β-[N-(N',N'-dimethyl-aminoethane)-carbamoyl]-cholesterol (DC-Chol), 1,2-bis(oleoyloxy-3-trimethylammonio-propane (DOTAP) (see, for example, WO 98/07408), lysinylphosphatidylethanolamine (L-PE), lipopolyamines such as lipospermine, N-(2-hydroxyethyl)-N,N-dimethyl-2,3-bis(dodecyloxy)-1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy) propyl-N,N,N-triethylammonium (DOTMA), DOSPA, DMRIE, GL-67, GL-89, Lipofectin, and Lipofectamine (Thiery et al. (1997) *Gene Ther.* 4:226-237; Felgner et al., *Annals N.Y. Acad. Sci.* 772:126-139, 1995; Eastman et al., *Hum. Gene Ther.* 8:765-773, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also encompassed are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

Host Cells

Recombinant host cells comprising a subject nucleic acid molecule may serve as a source of stable variant apoE protein of the invention. They also serve to propagate a subject nucleic acid. They further serve as test systems to analyze the effect of a variant stable apoE on effects associated with the presence of a stable apoE folding intermediate.

In some embodiments, of particular interest are mammalian cells that normally produce apoE, and cells that normally take up apoE from their environment. Examples of such cells include neuronal cells, microglial cells, and astrocytes. Immortalized neuronal cells, microglial cells, and astrocytes are also of interest.

Transgenic, Non-Human Animals

The present invention provides transgenic, non-human animals, particularly transgenic, non-human mammals that include, as a transgene, an exogenous nucleic acid that includes a coding region for a stable variant apoE polypeptide. The transgenic, non-human animals of the invention are useful for determining the effect of a stable variant apoE polypeptide on a pathology associated with apoE4. For example, by crossing a subject transgenic non-human animal with an animal model for Alzheimer's disease, the effect of the stable variant apoE on the disorder can be determined.

In many embodiments, the stable variant apoE-encoding transgene includes neuronal cell-specific regulatory elements such that the stable variant apoE is produced primarily in neuronal cells. However, the stable variant apoE-encoding transgene does not necessarily include neuronal cell-specific regulatory elements. In some embodiments, the stable variant apoE-encoding transgene is under transcriptional control of an inducible promoter.

Methods of generating transgenic, non-human animals, particularly transgenic, non-human mammals, are known in the art. See, e.g., U.S. Pat. Nos. 6,268,545; 6,255;554; 6,222,094; and 6,204,43; "Transgenic Animal Technology" C. A. Pinkert, ed. (1997) Acad. Press; "Gene Knockout Protocols" M. J. Tymms, et al., eds. (2001) Humana Press; and "Gene Targeting: A Practical Approach" A. L. Joyner, ed. (2000) Oxford Univ. Press.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

In some embodiments, the endogenous apoE gene is knocked out (e.g., rendered non-functional). Transgenic knockouts have a partial or complete loss of function in one or both alleles of the endogenous apoE gene.

The apoE gene transgene encodes stable variant apoE and is a genetically manipulated sequence as discussed above. The introduced sequence encodes a stable variant apoE polypeptide, and may further include additional coding sequences, including, e.g., nucleotides encoding a reporter protein (e.g., β-galactosidase, luciferase, green fluorescent protein, and the like). The transgene includes a stable variant apoE-encoding nucleotide sequence operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

DNA constructs for homologous recombination will comprise a nucleotide sequence encoding stable variant apoE, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. *Methods in Enzymology* 185:527-537 (1990).

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. See U.S. Pat. Nos. 5,387,742, 4,736,866 and 5,565,186 for methods of making transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week-old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allergenic or congenic grafts or transplants, or in in vitro culture.

Screening Assays

The present invention provides methods for identifying a compound that modulate the level and/or the structure and/or an activity of an apoE stable folding intermediate. Generally, the methods involve contacting a test agent with an isolated apoE stable folding intermediate or a native apoE polypeptide; and determining the effect, if any, of the test agent on the level and/or the structure and/or activity of an apoE stable folding intermediate. Test agents that have an effect in an assay method of the invention are candidates for treating an apoE4-associated disorder.

In some embodiments, the assays are cell-free assays performed in vitro. In other embodiments, the assays are cell-based assays performed in vitro. The assays may be performed in several different ways, and several different methods of detection may be employed to determine any effects of a test compound.

The terms "candidate agent," "test agent," "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Candidate agents are generally small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Screening may be directed to known pharmacologically active compounds and chemical analogs thereof, or to new agents with unknown properties such as those created through rational drug design.

Assays of the invention include controls, where suitable controls include a sample (e.g., a sample comprising native apoE or an apoE stable folding intermediate) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, anti-microbial agents, etc. may be used. The mixture of components is added in any order that provides for the requisite binding (e.g., of test agent to apoE or apoE stable folding intermediate). Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

A test agent of interest is one that reduces a level and/or an activity of an apoE stable folding intermediate by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent.

In some embodiments, the invention provides methods of identifying compounds that inhibit formation of an apoE stable folding intermediate. Formation of an apoE stable folding intermediate may be accomplished through reducing or increasing the concentration of a denaturant in a solution containing the apoE, as described above. As such, an exemplary assay comprises the following steps: a) contacting a native apoE polypeptide with a test agent in a solution; b) modifying the concentration of denaturant in the solution such that, in the absence of the test agent, an apoE stable folding intermediate is formed; and c) determining the effect, if any, of the test agent on the formation of apoE stable folding intermediate.

In other embodiments, a subject in vitro screening method identifies compounds that alter the structure of an apoE stable folding intermediate such that the stable folding intermediate has a more native-like structure or such that the stable folding intermediate is denatured and no longer exists as a stable folding intermediate. The methods generally involve contacting an apoE stable folding intermediate with a test agent, and determining the effect, if any, of the test agent on the structure of the apoE stable folding intermediate, compared to a control. Whether the test agent has an effect on the apoE stable folding intermediate can be determined using any known assay, as discussed above.

In other embodiments, a subject in vitro screening method identifies compounds that reduce a lipid binding activity of an apoE stable folding intermediate. These embodiments generally involve contacting an apoE stable folding intermediate with a lipid substrate and a test agent and determining the effect, if any, of the test agent on the binding of the apoE stable folding intermediate to the lipid substrate.

The effect of a test agent, on the binding of an apoE stable folding intermediate to a lipid substrate can be measured by any known method. In one non-limiting example, the ability of the stable folding intermediate to bind and disrupt vesicles, e.g. dimyristoylphosphatidylcholine vesicles, is measured. Vesicle disruption is measured using any known assay, including, but not limited to, release of encapsulated fluorescent dyes, turbidimetric clearing, and gel filtration assays. See, e.g., Lu et al. ((2000) *J. Biol. Chem.* 275 20775-20781).

In these embodiments, any suitable lipid substrate, such as lipid vesicles, in particular dimyristoylphosphatidylcholine vesicles may be used.

In general, conditions that promote formation of apoE stable folding intermediates include a pH of about 3.5 to about 4.5, e.g., about 4.0 and a denaturant concentration in the range of from about 2.0M to about 8.0M, e.g., from about 3.0M to 6.0M, or from about 3.5M to 5.0M. In one non-limiting example, e.g., where apoE4 is tested in an assay, assay conditions are performed in a solution that is pH 4.0 and contains about 3.75 M urea. In another non-limiting example, e.g., where apoE3 is tested in an assay, assay conditions are performed in a solution that is pH 4.0 and contains about 4.25 M urea.

The source of apoE for these assays may be any source of apoE, such as recombinant apoE, synthetic apoE, purified apoE, modified apoE or fragments of apoE such as a 22-kDa N-terminal fragment described above; so long as the apoE is substantially pure.

Determining the presence and/or the level of apoE stable folding intermediates is performed by any one of a number of methods for determining protein structure, which are well known in the art, including, but not limited to, far-ultraviolet circular dichroism (Morrow et al, *Biochemistry* 39:11657-11666 (2002)); fluorescence (Morrow et al., ibid); Fourier transfer infrared spectroscopy (e.g. as described by Oberg and Fink Anal. Biochem. 256:92-106 199); and dynamic light scattering.

In some embodiments, the in vitro screening methods are cell-based methods. Cell-based methods generally involve contacting a cell comprising a stable folding intermediate of apoE with a test agent; and determining the effect, if any, of the test agent on the level and/or activity of the apoE stable folding intermediate. The effect of the test agent on the activity of apoE stable folding intermediate can be determined by monitoring and/or measuring release of a dye encapsulated in the lysosomes. See, e.g., Ji et al. (2002) *J. Biol. Chem.* 277: 21821-21828. In general, the cells are incubated with a fluorescent dye for a period of time such that the dye is taken up by the lysosomes (e.g., one hour to about 16 hours), and release of the dye from the lysosomes is monitored. ApoE can be introduced into the cell by incubating the cell with apoE such that apoE is taken up by the cell. Alternatively, apoE can be introduced into the cell by introducing an apoE-encoding construct into the cell, such that the construct is expressed and apoE is produced. The construct can comprise an apoE-encoding nucleotide sequence under transcriptional control of an inducible promoter, such that the timing of apoE production is controlled by addition of an inducer. In some embodiments, Aβ is added to the cells.

Suitable cells include mammalian cells that normally produce apoE, as well as mammalian cells that do not normally produce apoE. In some embodiments, of particular interest are mammalian cells that normally produce apoE, and cells that normally take up apoE from their environment. Examples of such cells include neuronal cells, microglial cells, and astrocytes. Immortalized neuronal cells, microglial cells, and astrocytes are also of interest. In other embodiments, the cells do not normally produce apoE, but produce apoE after a construct comprising an apoE-encoding nucleotide sequence is introduced. Suitable mammalian cells include rodent and human cells and cell lines. Exemplary cells include COS-7 cells, Neuro-2a cells, and the like.

Therapeutic Agents

The invention provides agents that affect apoE stable folding intermediate levels and/or structure and/or activity, and compositions, including pharmaceutical compositions, comprising such agents. By reducing levels and/or altering the activity of apoE molten globules, the undesirable effects of apoE stable folding intermediates are reduced. Agents that reduce apoE stable folding intermediate levels and/or activity are useful in treating apoE4-associated neurological disorders. Agents that reduce apoE stable folding intermediate levels and/or activity are also useful in treating apoE-associated disorders related to cardiovascular disorders, e.g. high serum lipid levels.

Agents that reduce apoE molten globule levels and/or activity include agents that inhibit formation of apoE stable folding intermediates, agents that reduce the levels of apoE stable folding intermediates once they are produced, and agents that reduce a lipid binding activity of an apoE stable folding intermediate. Agents of interest are those that reduce an apoE stable folding intermediate and/or activity by at least about 10%, at least about 20%, at least about 25%, at least about 30%, at least about 40%, at least about 50%, at least about 60%, at least about 70%, at least about 80%, at least about 90%, or at least about 95% or more, up to 100%, compared to apoE stable folding intermediate levels and/or activity in the absence of the test agent.

Agents of interest are those that affect formation and/or activity of stable folding intermediates of any apoE isotype that forms stable folding intermediates.

Subject compositions may include a buffer, which is selected according to the desired use of the agent, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Methods of Reducing ApoE Stable Intermediate Levels and/or Activity

The present invention further provides methods of reducing the level and/or the activity of an apoE stable folding intermediate. The methods generally involve contacting a native apoE or an apoE stable folding intermediate with a subject agent, wherein the level and/or the activity of the apoE stable folding intermediate is reduced. The native apoE or the apoE stable folding intermediate can exist extracellularly or intracellularly, in vitro (e.g., in vitro in a cell, or in vitro outside of a cell or in a cell-free system); or in vivo.

In some embodiments, an agent that reduces the levels and/or activity of apoE stable folding intermediate renders the apoE molecule more "native" i.e. the apoE molecule is in a more native conformation. Thus, in some embodiments, the invention provides methods for converting apoE stable folding intermediate into native apoE, comprising contacting an apoE stable folding intermediate with an agent. In other embodiments, however, an agent that reduces the levels and/or activity of an apoE stable folding intermediate renders the apoE stable folding intermediate more "denatured" e.g., the apoE stable folding intermediate assumes a less native conformation. Thus, in some embodiments, the invention provides methods for converting apoE molten globules into more denatured apoE. In further embodiments of the invention, an agent reduces the levels and/or activity of apoE by inhibiting binding to a substrate, such as lipid. As such, the invention provides methods for inhibiting the activity of apoE, where the activity is, for examples, binding to a substrate, such as lipid.

Characteristics of "apoE levels" and "apoE activity" include, but are not limited to, binding affinity or efficiency of an apoE stable folding intermediate to lipids, absolute apoE stable folding intermediate levels and apoE stable folding intermediate levels in comparison to total apoE levels.

Methods of Treating ApoE-Related Disorders

The present invention provides methods of treating apoE4-related disorders (e.g., a disorder associated with apoE4 activity) in an individual. The methods generally involve administering to an individual having an apoE4-related disorder an effective amount of a compound that reduces the levels and/or activity of an apoE4 stable folding intermediate in the individual, e.g., in a neuronal cell, in an extracellular fluid, or in the bloodstream.

An "effective amount" of a compound is an amount that reduces a level and/or an activity of an apoE stable folding intermediate, e.g., in a neuronal cell, in an extracellular fluid, or in the bloodstream, in the individual, by at least about 10%, at least about 20%, at least about 30%, at least about 40%, at least about 50%, at least about 60%, at least about 70%, at least about 80% or more, compared to a levels and/or activity or an apoE stable folding intermediate in the individual, in the absence of the compound.

In some embodiments, the invention provides a method of treating Alzheimer's disease. In some embodiments, the method involves administering an inhibitor of apoE stable folding intermediate level and/or activity, where e.g. levels of neurofibrillary tangles in a neuronal cell are reduced.

Formulations, Dosages, and Routes of Administration

The invention provides formulations, including pharmaceutical formulations, comprising an agent that reduces a level and/or an activity of an apoE stable folding intermediate. In general, a formulation comprises an effective amount of an agent that reduces a level and/or an activity of an apoE stable folding intermediate. An "effective amount" refers to an amount that is sufficient to produce a desired result, e.g., reduction in a level and/or an activity of apoE stable folding intermediate, a reduction in neurofibrillary tangles, an improvement in learning, memory, a reduction of serum lipids etc. Generally, the desired result is at least a reduction in a level and/or an activity of an apoE stable folding intermediate as compared to a control. An agent that reduces a level and/or an activity of an apoE stable folding intermediate may delivered in such a manner as to avoid the blood-brain barrier, as described in more detail below. An agent that reduces a level and/or an activity of an apoE stable folding intermediate may be formulated and/or modified to enable the agent to cross the blood-brain barrier, as described in more detail below.

Formulations

In the subject methods, the active agent(s) may be administered to the host using any convenient means capable of resulting in the desired reduction in of a level and/or an activity of an apoE stable folding intermediate, reduction in any apoE4-associated neurological disorder, reduction in an apoE4-associated activity, reduction in serum lipids, etc.

Thus, the agent can be incorporated into a variety of formulations for therapeutic administration. More-particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation.

The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble-bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that reduces formation of neurofibrillary tangles and/or reduces the level of an apoE stable folding intermediate and/or reduces serum lipid levels can be administered in a single dose. Alternatively, a target dosage of an agent that reduces formation of neurofibrillary tangles and/or reduces the level of an apoE stable folding intermediate and/or reduces serum lipid levels can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces formation of neurofibrillary tangles and/or reduces the level or activity of an apoE stable folding intermediate and/or reduces serum lipid levels is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Crossing the Blood-Brain Barrier

The blood-brain barrier limits the uptake of many therapeutic agents into the brain and spinal cord from the general circulation. Molecules which cross the blood-brain barrier use two main mechanisms: free diffusion and facilitated transport. Because of the presence of the blood-brain barrier, attaining beneficial concentrations of a given therapeutic agent in the central nervous system (CNS) may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) Fed. Proc. 43:214-219; Baba et al. (1991) J. Cereb. Blood Flow Metab. 11:638-643; and Gennuso et al. (1993) Cancer Invest. 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) J. Med. Chem. 23:682-684; Pardridge (1991) in: Peptide Drug Delivery to the Brain; and Kostis et al. (1994) J. Clin. Pharmacol. 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, J-cyclodextrin, K-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) Proc. Natl. Acad. Sci. USA 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Subjects Suitable for Treatment with a Therapeutic Agent of the Invention

A variety of subjects are suitable for treatment with an agent identified by a method of the invention. Suitable subjects include any individual, particularly a human, who has an apoE4-associated disorder, who is at risk for developing an apoE4-associated disorder, who has had an apoE-associated disorder and is at risk for recurrence of the apoE-associated disorder, or who is recovering from an apoE4-associated disorder.

Such subjects include, but are not limited to, individuals who have been diagnosed as having Alzheimer's disease; individuals who have suffered one or more strokes; individuals who have suffered traumatic head injury; individuals who have high serum cholesterol levels; individuals who have Aβ deposits in brain tissue; individuals who have had one or more cardiac events; subjects undergoing cardiac surgery; and subjects with multiple sclerosis.

Neurological Diseases

Compounds found via an assay described herein are formulated to provide therapeutics for patients suffering from a wide range of neurological disorders. For instance, patients suffering from neurodegeneration or hypoxia may be treated. Neurodegeneration may result from a number of causes, including, but not limited to, Alzheimer's disease, trauma, viral infections, genetic enzyme deficiencies, age-related cognitive decline, and prion diseases. Viruses which may cause neurodegeneration include, but are not limited to, human immunodeficiency virus (HIV) and Epstein-Barr virus. Genetic enzyme deficiencies which may cause neurodegeneration include, but are not limited to, deficiency in β-N-acetylhexosaminidase which causes Tay-Sachs disease. Age-related cognitive decline is described, for instance, in Diagnostic and Statistical Manual of Mental Disorders, Fourth ed., Washington D.C. American Psychiatric Association (1994). Prion diseases include, but are not limited to, Kuru and Creutzfeldt-Jacob disease. Hypoxia is generally the result of stroke or is temporary and associated for instance with drowning, airway obstructions or carbon monoxide poisoning.

Neuron remodeling is also important in otherwise healthy patients. Therefore, compounds identified by the assay may be suitable for use prophylactically in patients who are heterozygous or homozygous for apoE4 but do not show overt symptoms of Alzheimer's disease or other neurodegenerative disorders.

Cardiovascular Diseases

Compounds found via an assay described herein are formulated to provide therapeutics for patients suffering from a wide range of cardiovascular disorders. For instance, patients suffering from coronary heart disease may be treated. Coronary heart disease may result from a number of causes, including, but not limited to hyperlipidemia (elevated lipid levels), hypercholesterolemia (elevated total or LDL cholesterol levels), hypertriglyceridemia, hyperlipoproteinemia, familial dysbetalipoproteinemia type III, familial hypercholesterolemia, xanthomas and tuberoeruptive xanthomas. Compounds found via an assay described herein may also be formulated to provide therapeutics for patients suffering from strokes, peripheral artery disease, and diabetes mellitus.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Formation and Characterization of ApoE Stable Folding Intermediates

Materials and Methods

Urea Denaturation

The 22-kDa fragments of apoE were purified as described in Morrow et al., 2000 (*Biochemistry* 39:1657-11666). Protein (400 µg/ml) was incubated overnight at 4° C. in buffer, 1 mM dithiothreitol, and freshly deionized urea at various concentrations. The buffer was 10 mM sodium phosphate for experiments at pH 7.4, and 20 mM sodium acetate for experiments at pH 4.0, which maintained the same ionic strength for both experiments. Circular dichroism measurements were made on a Jasco 715 or Applied Biophysics π-280 spectropolarimeter using a 1-mm pathlength cuvette. All experiments were performed under reducing conditions (25 mM dithiothreitol) at 25° C. Molar ellipticity ($[\theta]$) at 220 nm was calculated from the relationship $[\theta]=(MRW)(\theta_{220})/(10)(l)(c)$, where $\theta_{220}$ is the measured ellipticity at 220 nm in degrees, l is the cuvette path length (0.1 cm), and c is the protein concentration in g/ml and the mean residue weight (MRW) was 114. The denaturation curves at pH 4.0 were analyzed according to a three-state model as previously described by Barrick et al., 1993 (*Biochemistry* 32:3790-3796).

Proteolysis of the 22-kDa Fragment of ApoE

Pepsin (Sigma) was added to the 22-kDa fragment of apoE (0.1 mg/ml, 20 nM sodium acetate, pH 4.0) in 0, 3.75, or 4.75 M urea at a ratio of 10:1, 250:1 or 2000:1 (apoE:pepsin, w:w), respectively, and incubated at room temperature. At various time points, 500-µl aliquots were taken. Tris buffer and NaOH were added to inactivate pepsin, and the sample was dialyzed against 100 mM ammonium bicarbonate to remove the urea before lyophilization of the sample. The sample was then resuspended in a Tris-tricine sample buffer and analyzed by sodium dodecyl sulfate-polyacrylamide gel electrophoresis (SDS-PAGE) followed by transfer to a polyvinylidene fluoride membrane for amino-terminal sequencing (Perkin-Elmer Procise protein sequencer).

Analysis of the 22-kDa Fragment of ApoE4 by Infrared Spectroscopy

Solution-attenuated total reflectance FTIR was performed on the 22-kDa fragment of apoE4 (10 mg/ml, 10 mM cacodylate, pH 4.0, with or without 3.75 M urea) as described Oberg et al, 1998 (Anal. Biochem. 256, 92-106). The spectra were analyzed to estimate secondary structural content as described in Oberg et al, 1998 (Eur. J. Biochem. 258, 214-222) and Cabiaux et al, 1997 (Biophys. J. 73, 406-417).

Dynamic Light Scattering (DLS)

Scattering data were collected at 20° C. with a DynaPro-MS/X (Protein Solutions, Charlottesville, Va.). Samples of the apoE4 22-kDa fragment (0.5 mg/ml) were examined at pH 7.4 and 4.0 in the absence of urea and at pH. 4.0 in the presence of 3.75 M urea. Diffusion coefficients were determined from scattering data with the DYNAMICS autocorrelation analysis software (version 5.25.44, Protein Solutions). All data could be fitted multimodally, and essentially 100% of the scattering mass was attributed to a single low molecular weight component. The diffusion coefficient (D) and the hydrodynamic radius (Rh) are related by $Rh=kT/6\pi\eta D$. Viscosity (η) for the dilute sodium-acetate buffer was set to 1.0. The molecular mass (Mr) was estimated from the empirical relation Mr=(Rh·k)n, where k and n are parameters specific for the hydrodynamic model used. For globular proteins, k=1.68 and n=2.34. For nonspherical proteins, the Rh must be corrected by using the Perrin factor F determined from molecular dimensions. The apoE4 22-kDa fragment was approximated as a prolate ellipsoid with an axial ratio of 1:2.5 (F≈1.08). The pullulan model (an extended polysaccharide) was used to estimate hydrodynamic properties for random conformations (k=1.48, n=1.81). The derivations of the equations we used to calculate hydrodynamic properties are reviewed in Schmitz, 1990 (An Introduction to Dynamic Light Scattering by Macromolecules, eds, Academic Press, Boston).

Turbidimetric DMPC Clearance Assay

The kinetics of dimyristoylphosphatidylcholine (DMPC) large multilamellar vesicle remodeling was performed as described (Spolaore et al. (2001) Biochemistry 40:9460-9468) with slight modifications. Samples of apoE 22-kDa fragments were dialyzed into 5 mM DTT, 20 mM sodium acetate, pH 4.0 containing either 3.75 or 4.75 M urea at 4° C. and adjusted to final protein concentrations of 0.5 mg/mL. A solution of DMPC (Avanti Polar Lipids) in chloroform: methanol (1:1, v:v) was evaporated under a stream of argon and further desiccated under reduced pressure overnight. The dried DMPC film was resuspended in 20 mM sodium acetate, pH 4.0, containing either 3.75 M or 4.75 M urea. The concentration of DMPC was determined using an enzymatic colorimetric assay for phospholipids (Wako Chemicals) and diluted to a final DMPC concentration of 0.5 mg/mL. DMPC solution (400 µL) was added to a 1-cm pathlength quartz cuvette followed by the addition of buffer or protein solution with rapid mixing (200 µL). The turbidity of the solution was monitored at a wavelength of 325 nm using a Beckman DU-640 spectrophotometer. All solutions were maintained at a temperature of 24° C. before mixing and during data collection.

Results

Urea Denaturation

Figure 1B:
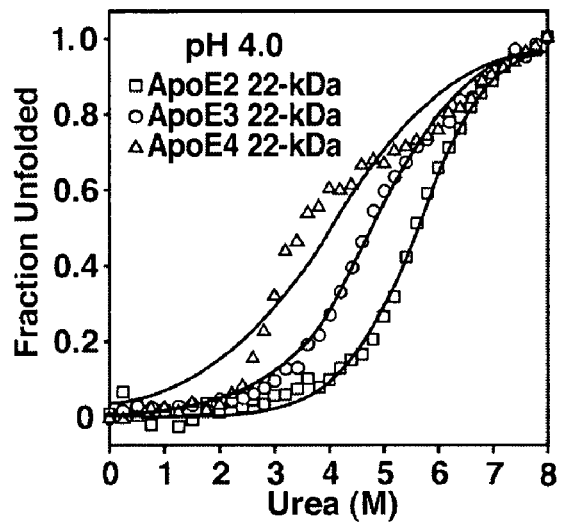
Figure 1C:
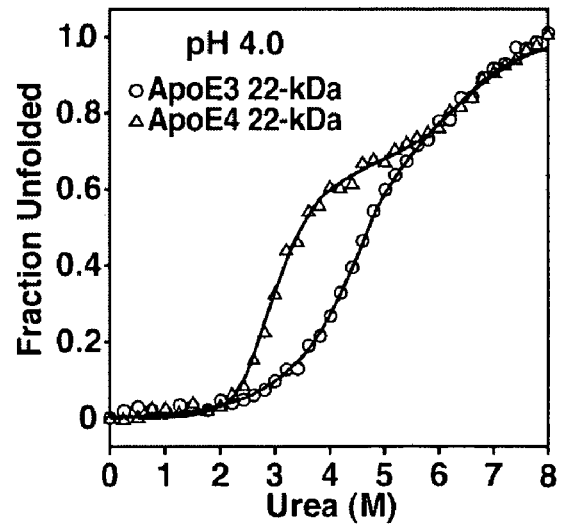

The 22-kDa fragments of apoE3 and apoE4 were examined by urea denaturation at pH 7.4 and pH 4.0. The unfolding of the fragments at various urea concentrations at pH 7.4 and 4.0, as shown in FIGS. 1A and 1B, was monitored by circular dichroism. Molar ellipticity ([θ]) at 220 nm was calculated from the relationship: [θ]=(MRW)(θ$_{220}$)/(10)(l)(c), where θ$_{220}$ is the measured ellipticity at 220 nm in degrees, l is the cuvette path length (0.1 cm), and c is the protein concentration in g/ml. A mean MRW of 114 was used. The denaturation curves at pH 7.4 reflected an apparent two-state denaturation. The midpoints of denaturation for the 22-kDa fragments of apoE3 and apoE4 were 5.2 M and 4.3 M urea (FIG. 1A). At pH 4.0, apoE4 and apoE3 displayed the same order of denaturation (apoE4>apoE3). However, there was a distinct plateau in the curves for both isoforms, suggesting the presence of a stable folding intermediate (FIG. 1B). As with guanidine denaturation, apoE2 was the most resistant to unfolding in urea and lacked an obvious plateau indicating that it did not form a folding intermediate (FIG. 1B.) The data in FIG. 1B were fitted to a 2-state model (unfolded/folded, solid lines overlaying the data). The poor fits to the apoE3 and apoE4 data further highlight the presence of stable folding intermediates in comparison to the reasonable fit obtained for the apoE2 data. Therefore, the data were analyzed according to a three-state model (native/intermediate/unfolded) (Barrick et al. (1993) Biochemistry 32:3790-3796), which gave excellent fits for the apoE3 and apoE4 isoforms (FIG. 1C) but did not give a better fit for apoE2 over the 2-state model.

Figure 2A:
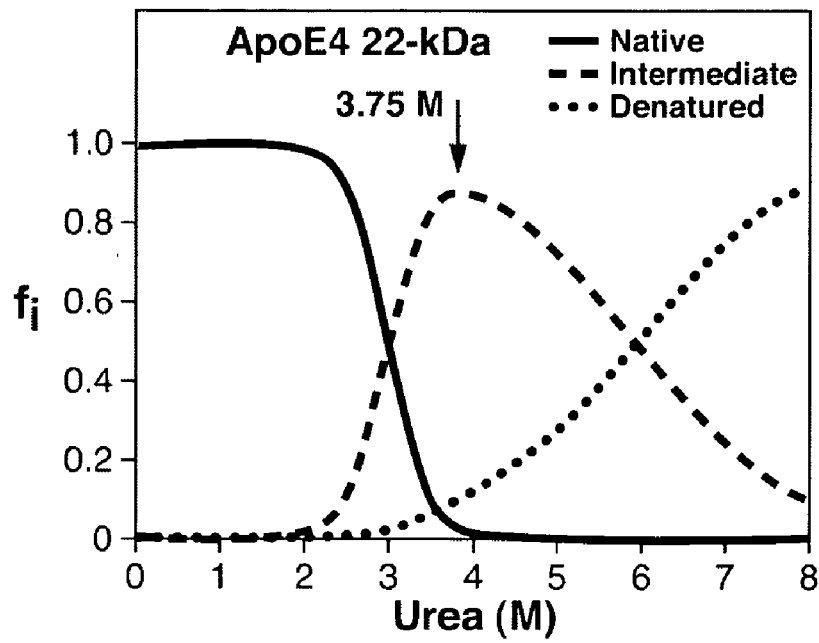
FIGS. 2A and 2B depict urea denaturation curves of the 22-kDa fragments of apoE3 and apoE4 at pH 4.
Figure 2B:
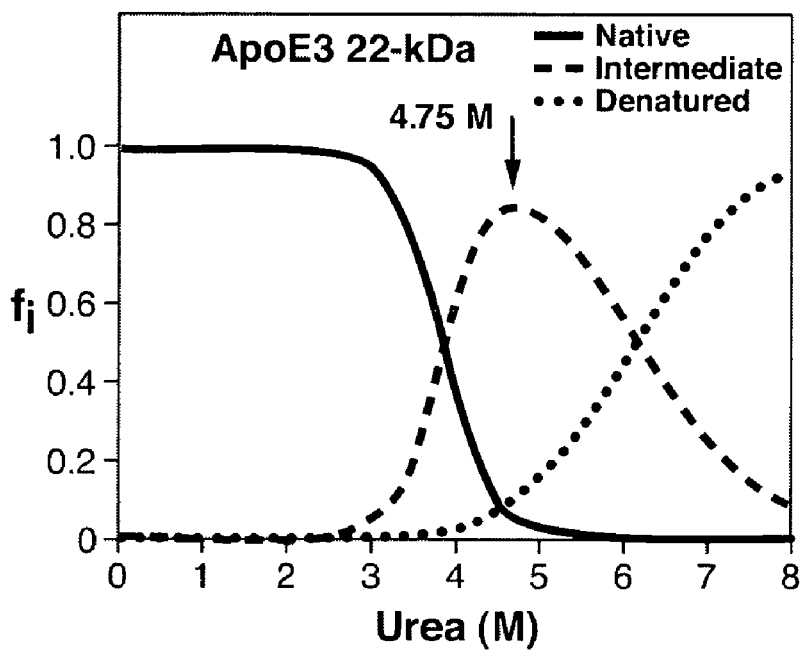

FIGS. 2A and 2B show the fraction of folded, intermediate and unfolded protein for apoE3 and apoE4 according to the three-state model. The concentration of urea at which the folding intermediate was at maximum concentration was 3.75 M for the apoE4 22-kDa fragment (≈90%) and 4.75 M for the apoE3 fragment (≈80%). These results demonstrate that in urea the folding intermediate is a stable thermodynamic state—the first criterion for a molten globule.

Pepsin Proteolysis

Since proteolysis is a sensitive probe for conformational changes in proteins, the apoE fragments were subjected to limited proteolysis with pepsin at low pH with or without urea and analyzed by SDS-PAGE and amino-terminal sequencing. In 0 M urea, there was one major fragment, which had the amino-terminal sequence of RQQTE, which corresponds to amino acids 15-19 in apoE. This sequence is at the flexible amino terminus of the 22-kDa fragment that is not resolved in the x-ray structure. Further addition of pepsin or longer digestion times did not produce smaller cleavage products under these conditions.

Digestion of the apoE4 22-kDa fragment in 3.75 M urea, the concentration at which the intermediate represents ≈90% of the mixture, revealed seven major bands. Bands (1-5) had the amino-terminal sequence GSK$^1$VE (SEQ ID NO:1), the same as that of recombinant apoE (it contains the novel Gly-Ser sequence at the amino terminus) (Morrow et al. (1999) Protein Expr. Purif. 16:224-230). Band 4 also contained a fragment with the amino-terminal sequence E$^{79}$EQLTP (SEQ ID NO:2). Band 6 had the amino-terminal sequence V$^{122}$QYRG (SEQ ID NO:3). Band 7 was rather broad and contained three fragments (A$^{124}$MLGQSTEE (SEQ ID NO:4); R$^{133}$VRLASHLR (SEQ ID NO:5); and V$^{116}$QYRGEVQA (SEQ ID NO:6)). Digestion of the apoE3 22-kDa fragment in 3.75 M urea yielded the same bands as the apoE4 digestion but with less proteolysis of the intact apoE3 fragment.

The bands after digestion of apoE3 and apoE4 in 4.75 M urea were similar to those obtained after digestion in 3.75 M urea, but there was less difference in extent of digestion. This result is consistent with the prediction, based on analysis of a three-state model, that similar amounts of the intermediate states from each isoform would be present in 4.75 M urea but not in 3.75 M urea. The increased sensitivity to pepsin digestion is also consistent with an altered conformation at low pH in the presence of urea—another characteristic of a molten globule. It is also important to note that there are a limited number of exposed pepsin cleavage sites, which is consistent with a limited structural or conformational reorganization of the apoE4 intermediate without complete loss of native structure.

Pepsin Digestion of a "Locked Bundle"

To determine if the four-helix bundle in the intermediate is opened or unfolded, we took advantage of a triple disulfide bond mutant that was used to test the hypothesis that the four-helix bundle opens, exposing the hydrophobic core, when apoE binds to lipid (Lu et al 2000 J. Bio. Chem 275, 20775-20781). This mutant was designed based on the x-ray structure of the 22-kDa fragment. Cysteine residues were substituted at sites in the bundle that were on opposite helices and within disulfide bond distances. Once formed, the three disulfide bonds effectively prevent the bundle from opening. The 22-kDa fragments of the triple disulfide mutant, apoE3, and apoE4 were digested with pepsin at pH 4.0 in 4.75 M urea, conditions under which both the apoE3 and apoE4 fragments are cleaved.

The triple disulfide bond mutant in which the four-helix bundle is effectively prevented from opening was digested overnight in 4.75.M urea at pH 4.0 in the nonreduced (Triple Mutant+Pepsin) and reduced forms (Triple Mutant+Pepsin) along with apoE3 and apoE4 control digestions. The extent of digestion was monitored by SDS-PAGE. The triple disulfide mutant was resistant to pepsin digestion (Triple Mutant+Pepsin). However, if the disulfide bonds were reduced during the digestion, releasing the helical constraints, the mutant was cleaved (Triple Mutant-R+Pepsin). This result supports the hypothesis that the four-helix bundle is at least partially opened in the folding intermediate.

Fourier Transform Infrared Resonance

Figure 3:
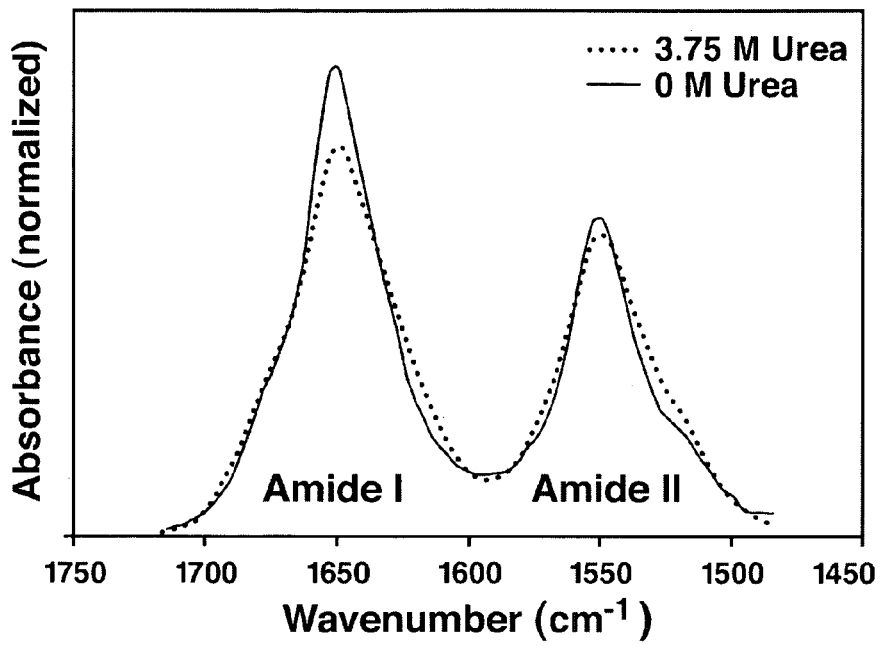
FIG. 3 depicts FTIR analysis of apoE4 22-kDa fragment.

We used an FTIR method to assess the secondary structure of the intermediate in urea. This method includes the subtraction of the urea background, as well as subtraction of absorbed (partially denatured) protein (Oberg et al (1998) Anal. Biochem. 256, 92-106). The apoE4 22-kDa fragment was analyzed at pH 4.0 in the presence or absence of 3.75 M urea (FIG. 3). Analysis in the amide I and II regions of the spectra was performed. ApoE4 22-kDa in 0 M urea displayed 75% α-helix and 3% β-sheet, consistent with the α-helical content estimated by circular dichroism (Aggerbeck et al (1988) J. Biol. Chem. 263, 6249-6258) and x-ray crystallography. In 3.75 M urea, apoE4 22-kDa displayed 46% α-helix and 17% β-sheet. Thus, the intermediate retains 61% of the native helical content, another criterion of a molten globule. In addition, it has a significant increase in β structure, which may promote aggregation and fibrillization.

Dynamic Light Scattering

DLS was used to determine the aggregation state of the intermediate. The measured hydrodynamic radii and estimated molecular weights are summarized in Table 1. The shape-corrected $M_r$ calculated for the reference sample apoE4 22-kDa fragment at pH 7.4 with no urea was 22 kDa. At pH 4.0 (no urea), the size distribution (polydispersity) was wider, and the $R_h$ was larger. Although the difference was not significant within the error of the experiment, it is reasonable to speculate that both the larger $R_h$ and the greater size distribution indicate a somewhat lower stability of the apoE4 22-kDa fragment at the acidic pH, consistent with its increased tendency to form an intermediate at pH 4.0. A small widening in the flexible and dynamic helix bundle, as indicated by crystallographic studies (Segelke et al. (2000) Protein Sci. 9:886-897), would not lead to a change in the helical content as determined from circular dichroism spectra and thus would still be compatible with a small increase in the $R_h$, indicating a flexing of the four-helix bundle at pH 4.0.

A more dramatic change was observed in the hydrodynamic behavior of the apoE4 22-kDa fragment at pH 4.0 in 3.75 M urea. $R_h$ increased significantly, but the size distribution remained narrow, indicating a well-defined intermediate species. Assuming a large contribution of random coil conformation in the intermediate, the Mr corresponding to the Rh for a random coil model was estimated to be ≈24 kDa, consistent with a monomeric species and no evidence of aggregation under these conditions.

TABLE I

Hydrodynamic radius and derived properties for the apoE4 22kDa fragment.

| pH | 7.4 | 4.0 | 4.0 |
|---|---|---|---|
| [urea] (M) | 0.0 | 0.0 | 3.75 |
| Hydrodynamic radius (nm, e.s.u.) | 2.40 ± 0.47 | 2.61 ± 0.67 | 3.93 ± 0.4 |
| Polydispersity (%)[a] | 19.5 | 25.5 | 12.5 |
| $M_r$ (kDa, globular estimate) | 26.1 | 31.7 | 82.8 |
| $M_r$ (kD[a], shape corrected)[b] | 21.8 | 26.5 | 24.2 |

[a]Polydispersity is a measure of the size distribution
[b]Prolate ellipsoid shape correction factor f = 1.08 used in calculation for columns 1,2. A random coil model was used for the calculation of $M_r$ in column 3.

Lipid Binding Abilities of the Three Isoforms

Figure 4:
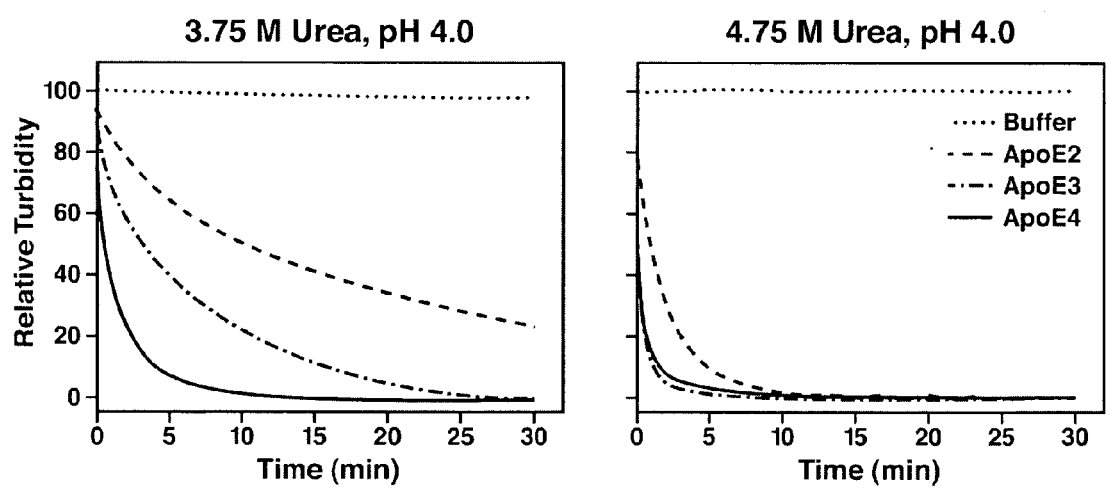
FIG. 4 depicts comparison of the lipid-binding activities of the apoE3 and apoE4 22-kDa fragments at pH 4.0.
Figure 5:
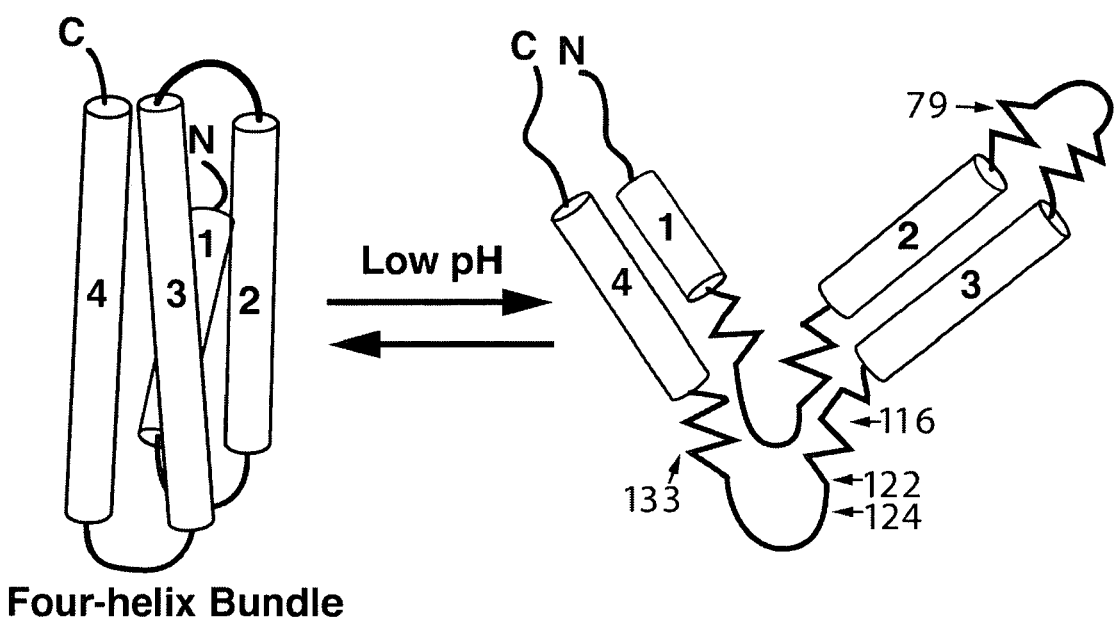
FIG. 5 depicts a model of the apoE4 22-kDa fragment in its molten globule state. The peptic cleavage sites that are exposed in the molten globule state are indicated by the small arrows.

The relative abilities of the three isoforms to bind and disrupt DMPC vesicles were determined at pH 4.0 in a turbidimetric clearing assay under urea concentrations where the intermediate species is highly populated for apoE4 and apoE3. It is important to note that while the carboxyl-terminal domain of apoE contains the major lipid binding determinants, the N-terminal 22-kDa domain also is capable of binding to lipid. Previous studies have indicated that the N-terminal 22 kDa-fragment clears with approximately half the rate as the intact protein at pH 7.4 (Segall et al. (2002) J. Lipid Res. 43:1688-1700). In the presence of 3.75 M urea, where the apoE4 22-kDa fragment has its maximum population of intermediate species (≈90%), apoE4 is more effective in clearing DMPC solutions than both apoE3 and apoE2 (FIG. 4). In 4.75 M urea, where apoE3 has its maximum population of intermediate species (≈80%) and apoE4 is close to its maximum population (≈80%), apoE3 and apoE4 have a similar rate of clearance, while apoE2 lags behind. At 4.75 M urea the relative clearance rate of apoE2 is closer to that of apoE4 and apoE3 than at 3.75 M urea. There are two reasons for this. First, the DMPC vesicles are smaller at 4.75 M urea than at 3.75 M, based on their relative scattering intensities. Thus, the lipid substrate is different at the two urea concentrations. Second, at 4.75 M the apoE2 is beginning to unfold, which would be predicted to increase its lipid-binding ability. The important point is that apoE2 still lags behind apoE4 and apoE3, which is consistent with its greater stability and absence of any significant concentration of a folding intermediate. Overall, the results are consistent with the enhanced ability of the intermediate species to remodel DMPC compared to the folded state.

It is evident from the above results and discussion that the subject invention provides an important new means for reducing the activity and/or levels apoE stable folding intermediates. Specifically, the subject invention provides a system for reducing the activity and/or levels of apoE stable folding intermediates, where the activity may be a lipid binding activity. As such, the subject methods and systems find use in a variety of different applications, including research, medical, therapeutic and other applications. Accordingly, the present invention represents a significant contribution to the art.

What is claimed is:

1. A composition comprising an isolated apolipoprotein E (i.e., apoE) stable folding intermediate, wherein the apoE stable folding intermediate is at least about 80% pure, wherein the apoE is apoE3 or apoE4, and wherein the stable folding intermediate is formed at a pH of from about 1.0 to about 5.0.

2. The composition of claim 1, wherein the apoE stable folding intermediate comprises an N-terminal fragment of apoE4.

3. The composition of claim 1, wherein the apoE stable folding intermediate is at least about 90% pure.

4. The composition of claim 1, wherein the apoE stable folding intermediate comprises an N-terminal fragment of apoE3.

5. The composition of claim 1, wherein the apoE stable folding intermediate is formed at a pH of from about 2.0 to about 4.0.

6. The composition of claim 1, wherein the apoE stable folding intermediate is formed at a urea concentration of from about 2 M to about 7 M.

7. The composition of claim 1, wherein the apoE is apoE4, and wherein the apoE stable folding intermediate is formed at a urea concentration of from about 3.5 M to about 4.5 M.

8. The composition of claim 1, wherein the apoE is apoE3, and wherein the apoE stable folding intermediate is formed at a urea concentration of from about 4.5 M to about 5 M.

9. The composition of claim 2, wherein the N-terminal fragment of apoE4 is about 22 kDa in size.

10. The composition of claim 4, wherein the N-terminal fragment of apoE3 is about 22 kDa in size.

* * * * *

UNITED STATES PATENT AND TRADEMARK OFFICE
CERTIFICATE OF CORRECTION

| | |
|---|---|
| PATENT NO. | : 7,432,355 B2 |
| APPLICATION NO. | : 10/626415 |
| DATED | : October 7, 2008 |
| INVENTOR(S) | : Weisgraber et al. |

Page 1 of 1

It is certified that error appears in the above-identified patent and that said Letters Patent is hereby corrected as shown below:

Please replace the Statement Regarding Federally Sponsored Research beginning on column 1, line 14, with the following revised statement:

STATEMENT REGARDING FEDERALLY SPONSORED RESEARCH

--This invention was made with government support under grant number RO1NS35939 awarded by the National Institutes of Health. The government has certain rights in this invention.--

Signed and Sealed this

Twenty-second Day of December, 2009

David J. Kappos
*Director of the United States Patent and Trademark Office*

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: synthetic peptide

<400> SEQUENCE: 1

Gly Ser Lys Val Glu
 1               5

<210> SEQ ID NO 2
<211> LENGTH: 6
<212> TYPE: PRT
<213> ORGANISM: Artificial Sequence
<220> FEATURE:
<223> OTHER INFORMATION: synthetic peptide

<400> SEQUENCE: 2

Glu Glu Gln Leu Thr Pro
 1               5

<210> SEQ ID NO 3
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Val Gln Tyr Arg Gly
 1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Ala Met Leu Gly Gln Ser Thr Glu Glu
 1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Arg Val Arg Leu Ala Ser His Leu Arg
 1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 6

Val Gln Tyr Arg Gly Glu Val Gln Ala
 1               5
```